United States Patent [19]

Abdel-Rahman

[11] Patent Number: 5,760,291
[45] Date of Patent: Jun. 2, 1998

[54] METHOD AND APPARATUS FOR MIXING COLUMN EFFLUENT AND MAKE-UP GAS IN AN ELECTRON CAPTURE DETECTOR

[75] Inventor: Mahmoud F. Abdel-Rahman, West Grove, Pa.

[73] Assignee: Hewlett-Packard Co., Palo Alto, Calif.

[21] Appl. No.: 706,900

[22] Filed: Sep. 3, 1996

[51] Int. Cl.$^6$ .......................................................... G01N 7/00
[52] U.S. Cl. .......................... 73/23.35; 73/23.42; 250/379
[58] Field of Search .............................. 73/863.71, 23.2, 73/23.22, 23.24, 23.33, 23.42, 23.35; 324/465; 250/374, 379, 381, 382, 386

[56] References Cited

U.S. PATENT DOCUMENTS

| | | | |
|---|---|---|---|
| 3,009,097 | 11/1961 | Strange | 324/33 |
| 3,247,375 | 4/1966 | Lovelock | 250/43.5 |
| 3,378,725 | 4/1968 | Bochinski et al. | 324/465 X |
| 3,444,722 | 5/1969 | Roof | 73/23.42 X |
| 3,566,107 | 2/1971 | Taylor et al. | 324/465 |
| 3,634,754 | 1/1972 | Lovelock | 324/465 |
| 3,668,382 | 6/1972 | Cohen et al. | 250/41.9 TF |
| 3,850,579 | 11/1974 | Dubsky | 23/254 EF |

(List continued on next page.)

OTHER PUBLICATIONS

Product Review –"Electron Capture Detection For GC", Analytical Chemistry, Jul. 1, 1995, pp. 439A–442A.

J.E. Lovelock –"The Electron Capture Detection–Theory And Practice", Journal of Chromatography, 99 (1974) 3–12.

J.E. Lovelock –"Electron Capture Detector–Theory And Practice II", Journal of Chromatography, 158 (1978) 123–138.

W.B. Knighton and E.P. Grimsrud –Linearization Of Electron Capture Detector Response To Strongly Responding Compounds, Analytical Chemistry, 1983, 55, 713–718.

W.B. Knighton and E.P. Grimsrud –"Physical Parameters Affecting The Quantitative Response Of The Constant Current Electron–Capture Detector", Journal of Chromatography, 288 (1984) 237–252.

(List continued on next page.)

*Primary Examiner*—Hezron E. Williams
*Assistant Examiner*—Jay L. Politzer
*Attorney, Agent, or Firm*—Mark Z. Dudley

[57] ABSTRACT

Electron capture detector for use with an effluent stream from a gas chromatograph includes an ionization chamber and a sample inlet system connected to the ionization chamber wherein the sample inlet system effects uniform fluid mixture of the effluent fluid and a make-up gas prior to entry of the fluid mixture into the ionization chamber. A preferred mixing device includes a column liner having a flow acceleration region wherein a localized reduction in the internal diameter of the liner causes momentary turbulence of the fluid mixture.

7 Claims, 6 Drawing Sheets

U.S. PATENT DOCUMENTS

| | | | |
|---|---|---|---|
| 4,019,863 | 4/1977 | Jenkins et al. | 23/232 E |
| 4,031,397 | 6/1977 | Cardillo | 250/423 |
| 4,063,156 | 12/1977 | Patterson | 324/465 |
| 4,203,804 | 5/1980 | Janning et al. | 202/121 |
| 4,260,884 | 4/1981 | Lovelock | 250/324 |
| 4,261,964 | 4/1981 | Scott et al. | 423/450 |
| 4,264,817 | 4/1981 | Neukermans et al. | |
| 4,304,997 | 12/1981 | Sullivan et al. | 250/379 |
| 4,308,242 | 12/1981 | Horton | 423/221 |
| 4,331,821 | 5/1982 | Schubart et al. | 570/96 |
| 4,383,839 | 5/1983 | Sisti et al. | 55/67 |
| 4,388,411 | 6/1983 | Lovelock | 436/149 |
| 4,517,394 | 5/1985 | Wang et al. | 568/948 |
| 4,651,008 | 3/1987 | Wells | 324/465 X |
| 4,670,220 | 6/1987 | Wells | 422/103 |
| 4,684,807 | 8/1987 | Wells | 324/465 X |
| 4,733,086 | 3/1988 | Simmonds | |
| 4,740,695 | 4/1988 | Simpson | |
| 4,851,683 | 7/1989 | Yang et al. | 250/339 |
| 4,887,464 | 12/1989 | Tannenbaum et al. | 73/153 |
| 4,994,096 | 2/1991 | Klein et al. | 55/20 |
| 4,995,222 | 2/1991 | Whitman et al. | 53/510 |
| 5,028,544 | 7/1991 | Rasulev et al. | 436/161 |
| 5,108,466 | 4/1992 | Klein et al. | 55/20 |
| 5,108,468 | 4/1992 | Ligon | 55/67 |
| 5,153,519 | 10/1992 | Wentworth et al. | 324/464 |
| 5,281,397 | 1/1994 | Ligon et al. | 422/89 |
| 5,302,325 | 4/1994 | Cheng | 261/76 |
| 5,472,645 | 12/1995 | Rock et al. | 261/79.1 |
| 5,479,022 | 12/1995 | Simon, Jr. | |
| 5,514,267 | 5/1996 | Machiya et al. | 210/170 |
| 5,567,885 | 10/1996 | Garside | 73/861.07 |

OTHER PUBLICATIONS

G. Wells –"A Micro–Volume Electron Capture Detector For Use In High Resolution Capillary Column Gas Chromatography", Journal of High Resolution Chromatography & Chromatography Communications, vol. 6, Dec. 1983, pp. 651–654.

G. Wells and R. Simon –"Evaluation Of Electron Capture Cell Designs For Use In High Resolution Capillary Column Gas Chromatography", Journal of High Resolution Chromatography & Chromatography Communications, vol. 6, Aug. 1983, pp. 427–430.

James J. Sullivan (Hewlett–Packard Co.) –"Approximation Of Electron Capture Response Factors For Highly Electrophilic Compounds", Journal of Chromatography, 87 (1973) 9–16.

J.J. Sullivan and C.A. Burgett (Hewlett–Packard Co.) –"Non–Linearity In Constant Current Electron Capture Detection", Chromatographia, vol. 8, No. 4, Apr. 1975, pp. 176–179.

J.J. Sullivan and D.H. Smith –"A New Linear Electron Capture Detector With Extended Dynamic Range", Hewlett–Packard Co. Technical Paper No. 49, given at The Pittsburgh Conference, Cleveland, 1972.

Sally S. Stafford and Bruce W. Hermann –"Design, Performance, And Use Of The Hewlett–Packard 5890 Series II Electron Capture Detector", Application Note 228–116, Hewlett–Packard Co., Jun. 1990.

| Injected Sample | Make-up Gas Flow Rate |
|---|---|
| —□— Lindane | 40 ml/min |
| —◈— Lindane | 80 ml/min |
| —▨— Lindane | 120 ml/min |

FIG. 6

METHOD AND APPARATUS FOR MIXING COLUMN EFFLUENT AND MAKE-UP GAS IN AN ELECTRON CAPTURE DETECTOR

FIELD OF THE INVENTION

This invention relates generally to ionization detectors and more particularly to an electron capture type of detector for use in detecting the constituent gases of a sample eluted from a gas chromatograph.

BACKGROUND OF THE INVENTION

Electron capture detectors for gas chromatography are well known in the art. For example, a review of such detectors is contained in an article entitled "Electron Capture Detectors for GC", by Debra Noble, *Analytical Chemistry*, Jul. 1, 1995, pp. 439A–442A. The electron capture detector is extremely sensitive to certain molecules such as alkyl halides, but is relatively insensitive to hydrocarbons, alcohols, ketones, etc. This type of detector features high sensitivity and high selectivity towards electrophilic compounds and is widely used for detecting trace amounts of pesticides in biological systems and in food products. Such compounds typically contain halogens which combine with free electrons in the detector. The resulting decrease in free electrons is monitored and used as an indication of the concentration of the test substances in a sample.

Figure 1A:
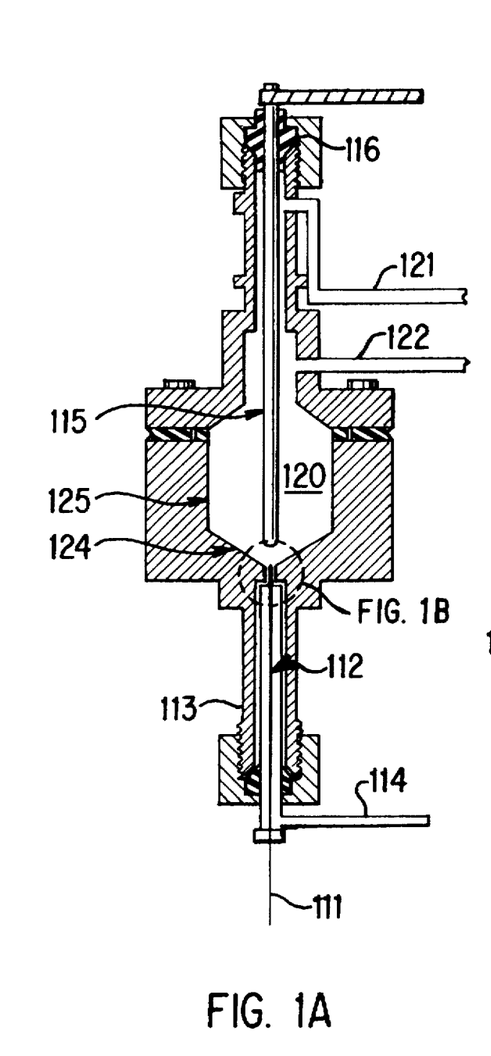
FIG. 1 is a schematic cross-sectional view of a prior art electron capture detector.
Figure 1B:
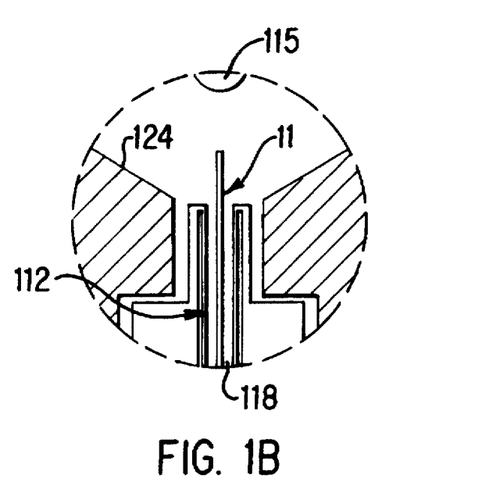

The electron capture detector can take several forms but all the forms are characterized by a flowthrough chamber containing spaced apart, insulated electrodes and a source of ionizing radiation. FIG. 1 illustrates the general design of a prior art electron capture detector 100, such as the electron capture detector installed in the HP 5890 Series II gas chromatograph, produced by Hewlett-Packard Co., Palo Alto, Calif. A generally cylindrical, electrically-pulsed metal electrode (anode) 115 is connected at its upper end to the upper body of the electron capture detector, separated therefrom by an insulator 116. The other end of the anode 115 projects into a lower region in a detection cell defined by an ionization chamber 120 having a grounded collector (cathode) 124. An outlet end of a separation column 111 is housed concentrically inside a fused silica liner 112 and an adapter 113. The placement of the column 111 in the liner 112 with respect to a make up gas feed line 114 is such that a passageway 118 is formed having an annular cross section between the inner wall of the liner 112 and the outer wall of the column 111. This passageway 118 in liner 112 is provided for passage of a make-up gas into the detector when, for example, the column 111 is a capillary column. The make-up gas is expected to be mixed with the effluent from the column 111. The top end of the chamber 120 is provided with side ports 121, 122. Side port 121 is typically connected to a pressurized supply of purge gas and side port 122 acts as a chamber vent.

The sample from the column 111 and the make-up gas from the passageway 118 are expected to enter the interior of the chamber 120 from below and travel upwards to the anode 115. Free electrons in the ionization chamber 120 are produced by radioactive beta emitters in the form of a foil or plating disposed inside the detector. Examples of such beta emitters are Tritium ($H^3$) and Nickel-63 ($Ni^{63}$). Thus, on the inner wall of the chamber 120 is a radioactive foil 125 which, in the illustrated example, is a $Ni^{63}$ radioactive source. The $Ni^{63}$ source ionizes the molecules of the make-up gas as it flows through the ionization chamber 120 and the electrons thus produced are caused to migrate to the anode 115, forming a pulsed electron current. This electron current becomes reduced if a sample containing electron-absorbing molecules is introduced; this loss of current can be amplified by an electrometer for analysis. Thus, when a sample component molecule comes into contact with the free electrons, the electrons may be captured by the sample molecule to create negatively charged ions. The voltage across the cell electrodes is pulsed to collect the remaining free electrons while the heavier ions are relatively unaffected and are swept with the carrier gas through the ionization chamber and out of the port 122

In the preferred constant-current, variable frequency mode of operation, the cell current is measured and compared to the reference current. The pulse rate is then adjusted to maintain a constant cell current. When a sample compound that captures electrons is present, the pulse rate increases. The pulse rate is converted to a voltage and recorded. Hence, the pulse rate is the detector output signal.

The response of the typical electron capture detector has been observed to be dependant upon many variables, such as the molecular composition of the analyte and its concentration, the cleanliness and the temperature of the detector cell, and the flow rates of the make-up gas and effluent. However, the behavior of the electron capture detector with regard many of these variables is not completely understood.

SUMMARY OF THE INVENTION

This invention accordingly relates generally to an improved electron capture detector for use in a high resolution gas chromatograph and in particular to a method and apparatus for the improving the uniformity and consistency of the fluid mixture provided to the ionization chamber of the electron capture detector. Such uniformity of the mixture of make-up fluid and the effluent thereby allows improved ionization of the sample molecules present in the effluent.

Substantial performance improvements in the detector response may be realized by improving the conditions for ionization of the sample molecules. Because the process of electron capture is based on the physical interaction between the sample molecules and the free electrons, the detector response is limited by the distribution of free electrons that are available for capture by the sample molecules. I have found that improving the uniformity of the distribution of the make-up gas with respect to the sample molecules is a prerequisite to providing a uniform distribution of free electrons to be captured by the sample molecules.

Accordingly, I have found that achieving a uniform mixing of the column effluent and the make-up gas, prior to their introduction to the ionization chamber, is essential to obtaining an accurate and consistent detector response signal. Furthermore, I have found that other improvements in the electron capture detector response are obtainable only after achieving the aforementioned uniform mixing of make-up gas and column effluent.

I have observed that only a partial mixing of column effluent and make-up gas occurs in the conventional electron capture detector. For example, with reference again to FIG. 1, the effluent gas stream and the make up gas stream typically does not achieve a uniform mixture. The degree of mixing is dependent on how far the column is inserted and the degree of concentricity of the effluent fluid stream with respect to the anode and the linear velocities of the effluent and the make-up gas. For example, the fast-moving effluent fluid stream is more likely to impinge upon, and then be reflected from, the anode and/or the ionization chamber walls without becoming uniformly mixed with the make-up gas. Consequently, I have found that consistently accurate response curves are not obtained from conventional detectors, and in particular, from detectors of differing construction, or from a single detector operated under differing configurations or at differing times. I have also found the effects of this phenomena to be especially troublesome at low column flow rates.

It is the purpose of this invention to solve this problem by providing an electron capture detector with a sample inlet system which requires the effluent stream and the make up gas stream to pass through a mixing device so as to achieve a substantially uniform fluid mixture.

It is a feature of the present invention that the mixing device is designed to ensure that the desired mixing of column effluent and make-up gas is substantially complete before the resulting fluid mixture enters the active volume of an ionization chamber.

It is another feature of the present invention that the outlet of the mixing device is designed to include a greater cross-section such that the resulting fluid mixture velocity is slowed in comparison to the effluent flow rate.

In another feature of the present invention, substantially no sample degradation is believed to occur in the mixing device as it is preferably made of deactivated quartz, fused silica, or glass and the mixing device is also kept at the same temperature as the ionization chamber. In prototype testing of an electron capture detector constructed according to the present invention, the detection of EPA pesticide standards (known as Mix-A and Mix-B) exhibited no sample degradation.

It is another feature of the present invention to provide a column adaptor having therein the associated mixing device so as to effect early mixing of the column effluent and the make-up gas at a flow region that is upstream of the ionization chamber. The mixing device preferably includes a liner having a flow acceleration region. The flow acceleration region is preferably provided as a localized reduction in the internal diameter of the liner, in a fashion that causes the make-up gas and the effluent fluid stream to be accelerated to turbulent condition.

It is another feature of the present invention to provide the localized reduction in the internal diameter of the liner in a fashion that also provides a column end stop, thus making it easy to locate the end of capillary column with respect to the flow acceleration region.

In the preferred embodiment of the present invention, the above and other features are achieved by providing an electron capture detector having an ionization chamber and a sample inlet system connected to the ionization chamber for effecting uniform mixing of an effluent fluid and a make-up gas at a flow region located upstream of the ionization chamber. In the preferred embodiment, the sample inlet system includes a mixing device and, in a particularly preferred embodiment, a column liner having a flow accelation region. Such region is preferably implemented by a localized reduction in the internal diameter of the liner. Preferably, the outlet end of the column is inserted into the liner to a point adjacent the localized reduction. Such a region also serves as a column end stop to prevent contact between the anode and the the column. The sample molecules and the make-up gas are thereby caused to flow through the flow acceleration region, thus producing a substantially uniform fluid mixture. The mixture of column effluent and make-up gas is achieved in the preferred embodiment even at very low flow rates (e.g.; 10 milliliters per minute of make-up gas and 1 milliliter per minute of column flow). As will be described below with reference to FIG. 6, consistent detector response curves may be then achieved that would otherwise be unreliable. Such consistency is believed to be unobtainable in an electron capture detector constructed according to the prior art.

Another advantage is that the ionization chamber is less subject to contamination, as more of the heavy oils and high boiling point contaminants are retained in the liner. The tasks of cleaning or replacement of the liner are also easier to perform in comparison to such tasks when performed on the ionization chamber (because, for example, the ionization chamber contains radioactive material). Also, the preferred localized reduction in the internal diameter of the liner prevents the passage of most fragments of the column into the ionization chamber.

The teachings of this invention apply to any detector operating on ionization of a fluid mixture, such as a helium ionization detector, argon ionization detector, and other electron capture detectors having either radioactive or non-radioactive electron sources.

DETAILED DESCRIPTION OF THE PREFERRED EMBODIMENTS

The apparatus and methods of the present invention may be employed in particular to improve the detection of an analyte that may be present in a variety of fluids. Gases are the preferred fluids according to the practice of the present invention, and therefore the following description of the invention will include a description of the arrangement, construction, and operation of a novel electron capture detector for use in a gas chromatographic analytical system (hereinafter, a chromatograph).

Embodiments of the invention described herein are contemplated for use as a temperature-controlled, constant-current, pulse-modulated electron capture detector in a gas chromatograph. The preferred operation of the contemplated detector with respect to a conventional gas chromatograph may be understood as follows. In a chromatographic separation of a given sample compound, a sample is injected with a pressurized carrier gas into a separation column and the column effluent is directed as a fluid stream into the electron capture detector. One or more pneumatic manifold assemblies are envisioned, each of which serves in part to control and redirect a plurality of gas flows, including the carrier gas and a plurality of detector gases of appropriate types such as air, hydrogen, and make-up gas. Accordingly, the pneumatic manifold may be operated to effect a modulation of any of the aforementioned gas flows, and in particular to supply modulated purge gas flow and make-up gas flow to the electron capture detector described hereinbelow. Aspects of such fluid supply in the embodiments illustrated in FIGS. 2 et seq. is preferably provided via electronic pneumatic control (EPC). For further details of electronic pneumatic control techniques, one may consult, for example. Klein, et al., U.S. Pat. No. 4,994,096 and U.S. Pat. No. 5,108,466, the disclosures of which are incorporated herein by reference.

As illustrated in FIGS. 2-5, a preferred embodiment 200 of an electron capture detector constructed according to the invention includes an upper body 210, anode 212, flow guide 220, curved washer 230, seal 240, lower body 250, and adapter 260. The upper body 210 includes an anode tube 213 that defines a central bore 214 for accommodating the anode 212 in a spaced, concentrically located position therein. The flow guide 220 and an electrically insulating insert (not shown, but typically mounted in the upper end of the central bore 214) are preferably formed of high purity alumina to ensure that the anode 212 is properly positioned and electrically isolated from the upper body 210.

Figure 2:
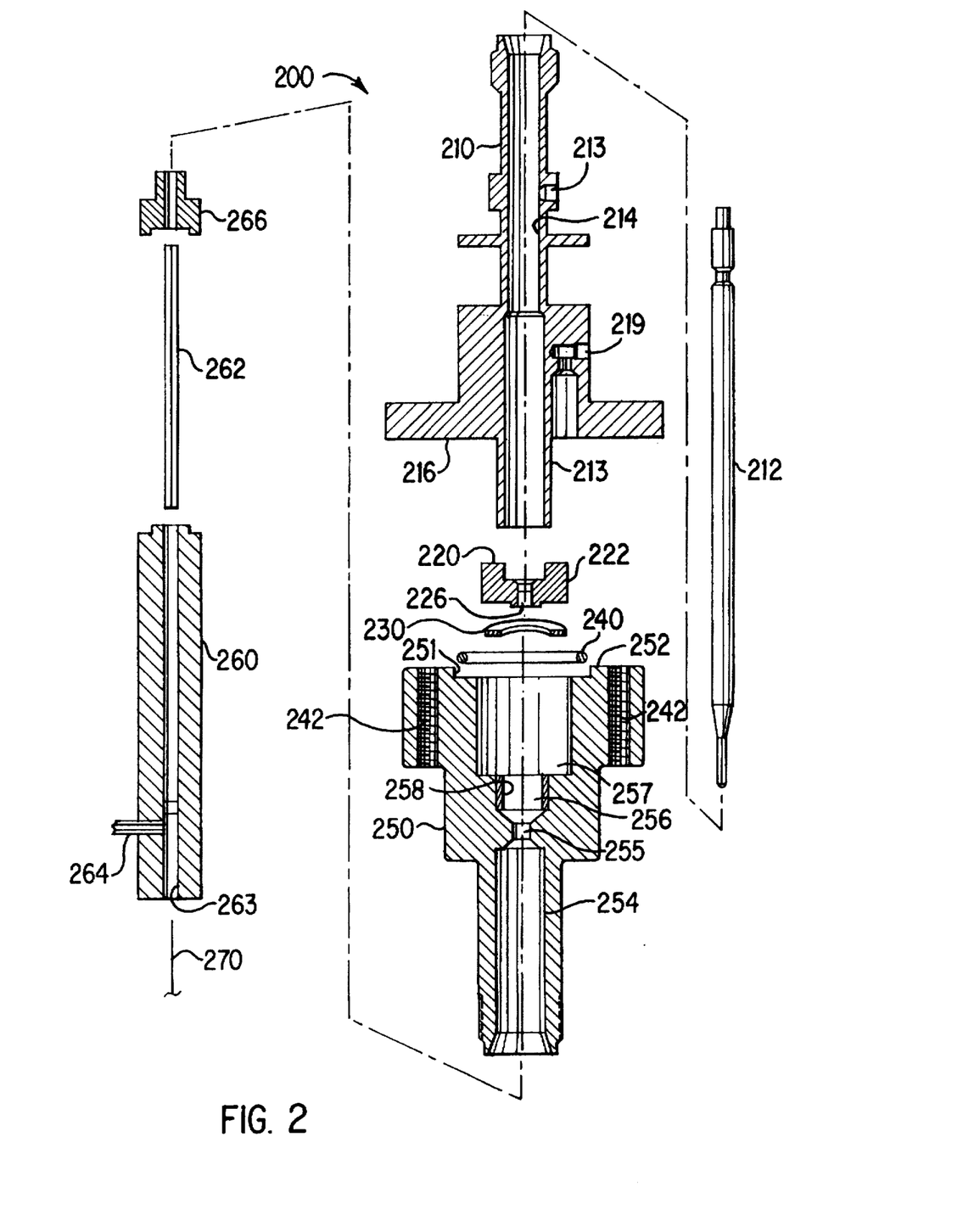
FIG. 2 is an exploded cross-sectional view of an electron capture detector of the present invention.

The lower body 250 includes a recess 251 in an interface 252 for receiving the seal 240 and for receiving a corresponding mating surface 216 on the upper body 210 is operable as a collector electrode. The lower body 250 includes a plurality of coaxially displaced, interconnected interior chambers which are in fluid communication therebetween: a central bore 254, a cap relief 255, an ionization chamber 256 having therein a radioactive source 258, and anode chamber 257. The curved washer 230 and flow guide 220 are locatable in the anode chamber 257 such that the uppermost surface of the flow guide 220 is closely fits onto the opposing surface of the anode tube 213. The upper body 210 also includes a purge flow inlet 218 which communicates with the central bore 214 and a purge flow outlet 219 which communicates with the anode chamber 257. Hermetic sealing between the mating surfaces 216, 252 is provided by compression of the seal 240 by appropriate clamping means such as screws extending through screw bores 242 into suitable receiving means (not shown) that may be located on or in the upper body 210. The upper body 210, lower body 250, and certain components therein (such as the curved washer 230) are preferably constructed of inert, heat resistant material such as stainless steel. The adapter 260, upper body 210, and lower body 250 may be heated to a selected temperature by means (not shown) as known in the art.

Figure 4:
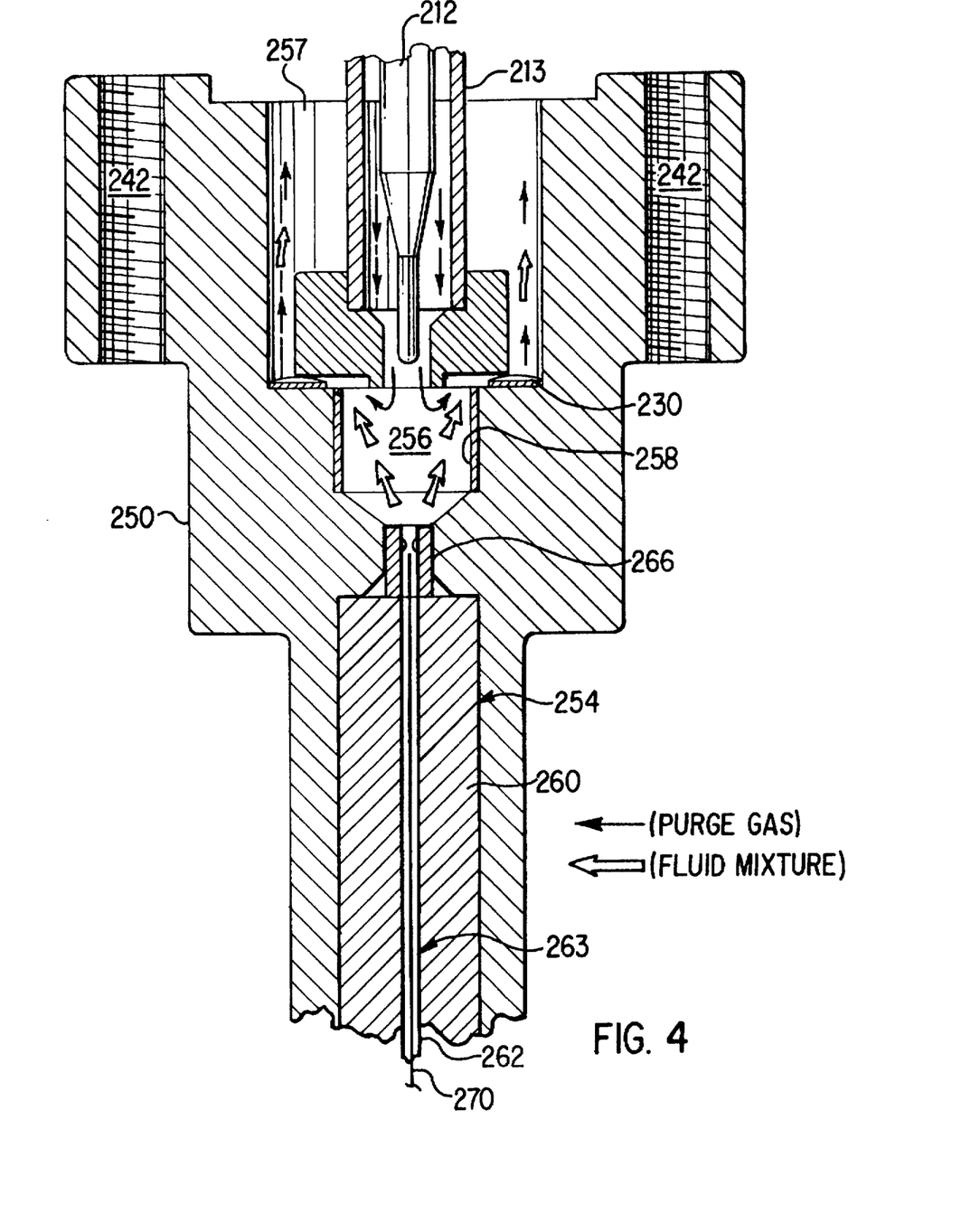
FIG. 4 shows an inlet system operable in the electron capture detector of FIG. 2.

An outlet end of a chromatographic column 270 is positioned in a liner 262 and the column/liner assembly is located in the central bore 263. Gas to be analyzed, such as the effluent (E) from the chromatographic column 270 is conducted within the column 270. Make-up fluid (NA) is thereafter supplied into the central bore 263 and into a central bore of the liner 262 by a make-up gas feed 264. A fluid mixture (F) composed of a substantially uniform mixture of the make-up gas (M) and the column effluent (E) are then passed into the central bore 254 from an adapter cap 266. Thus, when the adapter 260 is fully inserted into the central bore 254, the fluid mixture (F) exits the cap 266 and immediately enters into the ionization chamber 256.

Figure 3A:
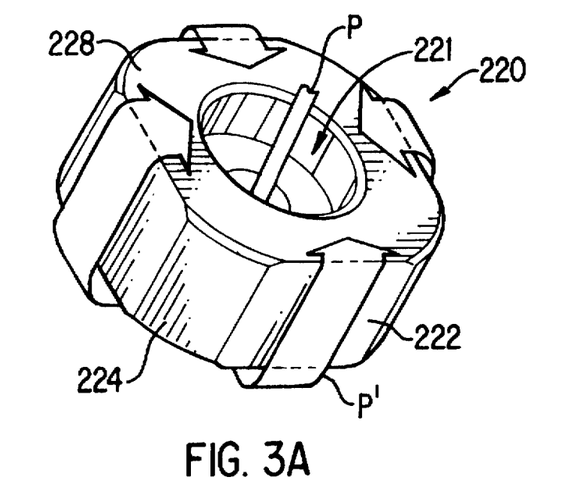
FIGS. 3A, 3B are perspective cross-sectional views of a preferred design for a flow guide for concealing the anode in the detector shown in FIG. 2.
Figure 3B:
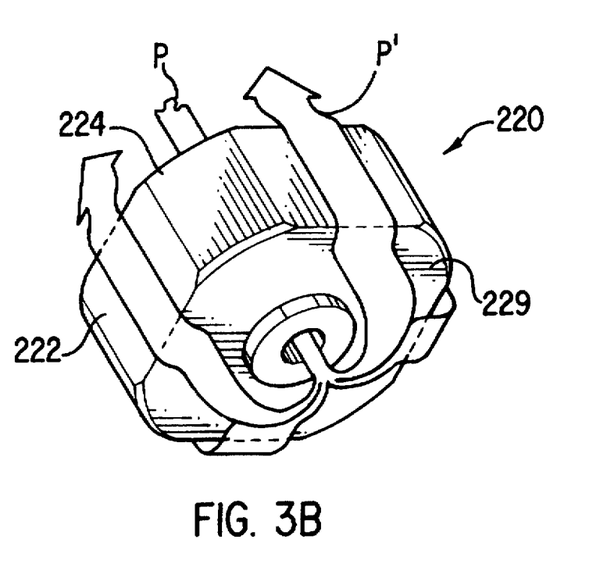

The flow guide 220 is located at the uppermost portion of the ionization chamber 250 to effect an uppermost boundary to the active volume of the ionization chamber 256, the latter being defined as the region from which electrons are collected for measurement. Hence the active region is situated below the flow guide 220, thereby separating the anode 212 from the active volume. For this purpose, the flow guide 220 is made of a highly insulative material, such as a high purity alumina composition marketed ss AL-300 and available from Wesgo/Duramic Precision Engineering Ceramics, Fairfield, N.J. The flow guide 220 is generally shaped like a disk, having a generally cylindrical section, upper and lower major surfaces 228, 229, side walls of alternating flat sections 222 and curved sections 224, and a recessed section 221 at its upper major side having an interior diameter sized for engaging and closely fitting a portion of the bottom exterior of the anode tube 213. The flow guide 220 is thus sized such that the curved sides 224 are sealing engaged with the interior of the anode chamber 257 when the flow guide 220 slides into the anode chamber 257. However, the presence of the curved washer 230 and the flat sides 222 allow the passage of purge gas (P) that originates from the purge flow inlet 218 and travels through the central bores 214 and 226 so as to be redirected (illustrated as purge gas P') over the lower major surface 229 of the flow guide 220. The lower major side 229 of the flow guide 220 faces into the ionization chamber 256 and thus towards the outlet end of the column/liner assembly.

The ionization chamber 256 has a cup-shaped section with the radioactive source 258 on its side wall being so designed and positioned such that the fluid mixture (F) can pass upwardly into the ionization chamber 256 for subsequent ionization of the sample molecules that are present in the fluid mixture (F). Further flow of the fluid mixture (F) is partially constrained by the lower major surface 229 of the flow guide 222 and by a fluid barrier provided by the purge gas flow (P') from a central bore 226 in the flow guide 222. That is, the fluid mixture (F) is prevented from contacting the anode 212 and is made to exit the ionization chamber 256 along the flat portions 222 of the side wall of the flow guide 222. Thus, the anode 212 is not actively swept by the fluid mixture (F). As a result, the anode 212 is effectively separated by the flow guide 220 from the fluid mixture (F) and the potential for contamination of the anode 212 by compounds in the fluid mixture is greatly reduced.

Figure 5:
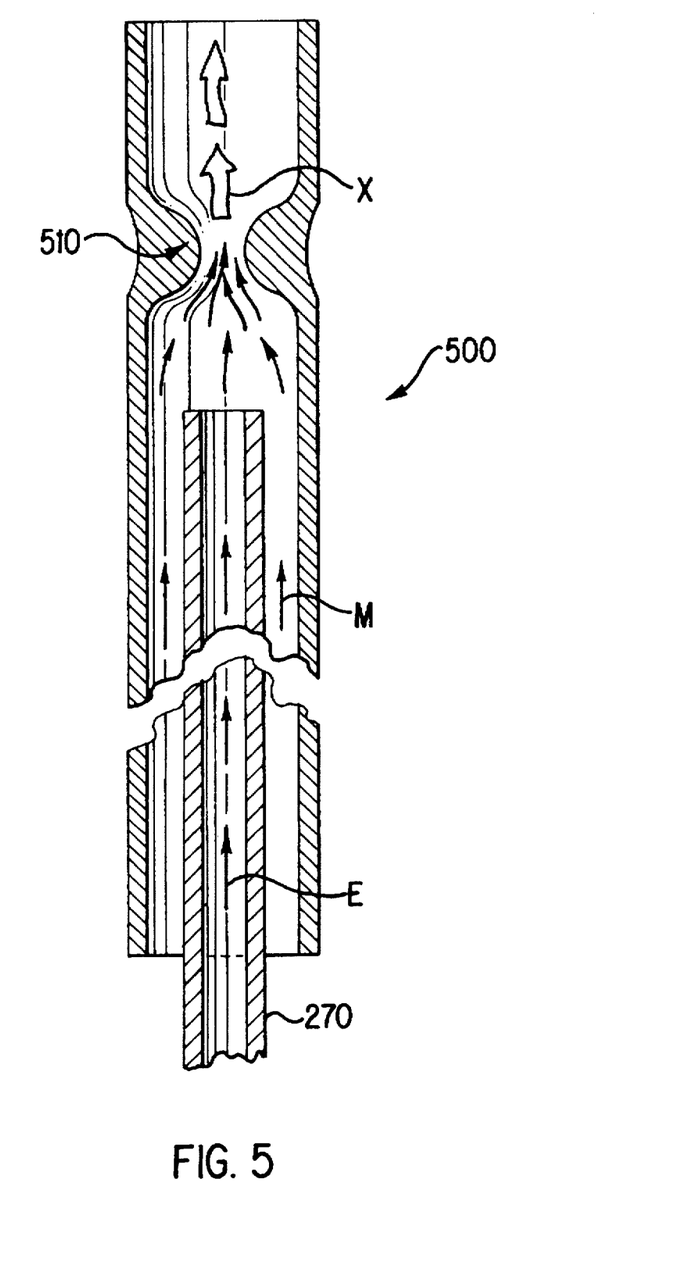
FIG. 5 is a cross-sectional view of an embodiment of a column liner constructed according to the invention to include a flow acceleration region for effecting a uniform mixture of column effluent and make-up gas.

As illustrated in FIG. 5, the desired mixing of the effluent and make-up gas is preferably implemented by a mixing device provided in the form of a hollow, tubular liner 500 formed of deactivated quartz and having a flow acceleration region 510 wherein the make-up gas and the effluent are subject to a momentary but substantial increase in velocity, thus causing turbulent flow within the flow acceleration region 510. The desired turbulent flow provides a substantially uniformly mixed product of the effluent (E) and the make-up gas (M). The flow acceleration region 510 is preferably provided by localized reduction of the internal diameter (I.D.) of the liner to a value that is approximately one-half to one-quarter of the average internal diameter. In one prototype of the liner 500, successful mixing was effected by a reduction of an average internal diameter of approximately 1000 micrometers to approximately 300 micrometers.

Another preferred aspect of the illustrated embodiment is that the portion of the liner 500 that is located downstream from the flow acceleration region 510 include a sufficiently large internal diameter such that the rate of flow of the fluid mixture (F) is slowed in comparison to the flow rate of the effluent (E). The relatively slow rate of entry of the fluid mixture (F) encourages a more uniform distribution of the sample molecules in the ionization chamber as the fluid mixture (F) flows into the ionization chamber 256.

Figure 6:
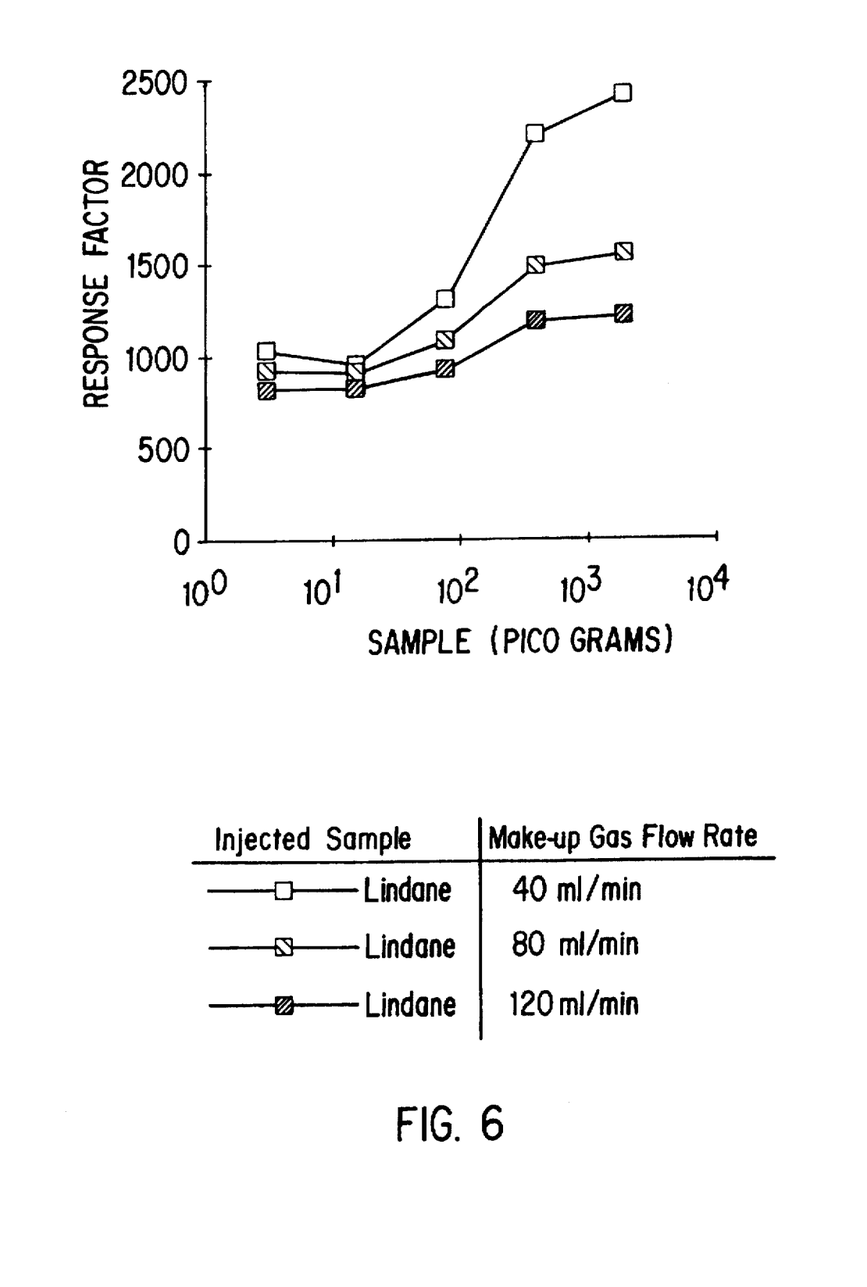
FIG. 6 is a graph showing experimental verification of the benefits of the present invention in a prototype of the electron capture detector of FIG. 2.

As illustrated in FIG. 6, improved quantitative results are represented in a response curve obtained from the ECD 100 illustrated in FIG. 1(i.e., the ECD installed in the HP 5890

Gas Chromatograph) which was modified to include a sample inlet system having a prototype version of the illustrated liner 500. The illustrated response curve indicates the relationship between an injected sample amount and the resulting area count in the detector response. The detector response factor is considered to be the detector response per unit sample. The illustrated curves exhibit: (a) in the concentration mode of operation, the detector response factor follows a linear decrease in response to an increase in the flow rate of the fluid mixture (F); and (b) in the coulometric mode of operation, the detector response factor is generally independent of the flow rate of the fluid mixture (F).

What is claimed is:

1. An electron capture detector for use with a gas chromatography column and a source of make-up gas, comprising:

an ionization chamber having an entrance opening;

sample inlet system operably connected between said column and the entrance opening for receiving column effluent and a fluid stream of the make-up gas and for directing a fluid mixture of column effluent and make-up gas to flow through said entrance opening into said ionization chamber, wherein said sample inlet system includes a mixing device for receiving the column effluent and the fluid stream of the make-up gas and for providing therefrom the fluid mixture as a substantially uniform mixture of said column effluent and make-up gas fluid stream and wherein the sample inlet system further comprises an adapter having a liner disposed therein, the liner having an internal bore for receiving an outlet end of the column concentrically therein, and wherein the mixing device is integrated in the liner;

an electron source associated with said ionization chamber for generating a plurality of electrons in said fluid mixture, whereby the presence of electron-capturing species in the fluid mixture may react with the electrons to form negative ions; and first and second spaced electrode means located with respect to said fluid mixture for detecting a subsequent variation in the electron concentration in the fluid mixture.

2. The electron capture detector of claim 1, wherein the mixing device further comprises a flow acceleration region in the internal bore of the liner, wherein at least one of the effluent and the make-up gas is subject to a momentary and rapid increase of flow velocity to induce turbulence.

3. The electron capture detector of claim 2, wherein the flow acceleration region in the liner further comprises a localized reduction in the internal diameter of the liner, wherein at least one of the effluent and the make-up gas are subject to turbulent flow at the localized reduction.

4. The electron capture detector of claim 3, wherein the liner has an average internal diameter and the localized reduction is selected to be a value within the range of one-quarter to one-half of the average internal diameter.

5. The electron capture detector of claim 3, wherein the liner has an internal diameter of approximately 1000 micrometers and the localized reduction has an internal diameter of approximately 300 micrometers.

6. The electron capture detector of claim 1, wherein the liner is composed of a material selected from the group of quartz, fused silica, and glass.

7. Method for electron capture detection for use with a gas chromatography column and a source of make-up gas, comprising the steps of:

providing an ionization chamber having an entrance opening and an exit opening;

providing a sample inlet system operably connected between said column and the entrance opening for receiving column effluent and a fluid stream of the make-up gas and for directing a fluid mixture of column effluent and make-up gas to flow through said entrance opening into said ionization chamber, wherein said sample inlet system includes a mixing device for receiving the column effluent and the make-up gas and for providing therefrom the fluid mixture as a substantially uniform mixture of said column effluent and make-up gas fluid stream stream and wherein the sample inlet system further comprises an adapter having a liner disposed therein, the liner having an internal bore for receiving an outlet end of the column concentrically therein, and wherein the mixing device is integrated in the liner;

operating an electron source associated with said ionization chamber for generating a concentration of electrons in said fluid mixture, whereby the presence of electron-capturing species in the fluid mixture may react with the electrons to form negative ions; and locating anode electrode means and collector electrode means with respect to said fluid mixture for detecting a subsequent variation in the electron concentration in the fluid mixture.

\* \* \* \* \*